United States Patent
Assaker et al.

(10) Patent No.: US 6,565,569 B1
(45) Date of Patent: *May 20, 2003

(54) BACKBONE OSTEOSYNTHESIS SYSTEM WITH CLAMPING MEANS, IN PARTICLULAR FOR ANTERIOR FIXING

(75) Inventors: Richard Assaker, Kain (BE); Frédéric Conchy, Saint-Medard-d'Eyrans (FR); Régis Le Couëdic, Cestas (FR)

(73) Assignee: Stryker Spine (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/674,196

(22) PCT Filed: Apr. 29, 1999

(86) PCT No.: PCT/FR99/01020

§ 371 (c)(1),
(2), (4) Date: Feb. 1, 2001

(87) PCT Pub. No.: WO99/55247

PCT Pub. Date: Nov. 4, 1999

(30) Foreign Application Priority Data

Apr. 29, 1998 (FR) ............................................. 98 05387
Oct. 9, 1998 (FR) ............................................. 98 12662

(51) Int. Cl.⁷ .............................................. A61B 17/70
(52) U.S. Cl. .............................. 606/61; 606/72; 606/73
(58) Field of Search .............................. 606/61, 60, 69, 606/70, 72, 73; 411/389, 537, 400, 395

(56) References Cited

U.S. PATENT DOCUMENTS

| | | | |
|---|---|---|---|
| 4,289,123 A | | 9/1981 | Dunn |
| 4,987,892 A | * | 1/1991 | Krag et al. .................... 606/61 |
| 5,108,395 A | | 4/1992 | Laurain |
| 5,147,360 A | | 9/1992 | Dubousset |
| 5,380,324 A | | 1/1995 | Müller et al. |
| 5,613,968 A | | 3/1997 | Lin ............................... 606/61 |
| 5,628,740 A | * | 5/1997 | Mullane ....................... 606/61 |
| 5,662,652 A | | 9/1997 | Schäfer et al. |
| 5,683,391 A | | 11/1997 | Boyd |
| 5,713,898 A | | 2/1998 | Stücker et al. |
| 5,938,663 A | * | 8/1999 | Petreto ........................ 606/61 |
| 6,004,322 A | * | 12/1999 | Bernstein .................... 606/61 |
| 6,123,706 A | | 9/2000 | Lange |
| 6,132,431 A | | 10/2000 | Nilsson et al. |
| 6,299,614 B1 | | 10/2001 | Kretschmer et al. |
| 6,328,739 B1 | * | 12/2001 | Liu et al. ..................... 606/61 |
| 6,423,064 B1 | * | 7/2002 | Kluger ........................ 403/373 |

FOREIGN PATENT DOCUMENTS

| | | | |
|---|---|---|---|
| DE | 94 12 744 | 7/1995 | |
| DE | 4433360 | * 1/1996 | .................. 606/61 |
| DE | 94 12 744 U1 | 1/1996 | |
| DE | 44 33 360 | 2/1996 | |
| DE | 195 34 136 | 3/1996 | |
| DE | 297 12 697 | 9/1997 | |
| EP | 0 726 064 A2 | 8/1996 | |
| FR | 2 244 446 | 9/1973 | |
| FR | 2 697 744 | 5/1994 | |
| FR | 2731344 | 9/1996 | |
| WO | WO 94/06360 | 3/1994 | |
| WO | WO 96/27340 | 9/1996 | |

* cited by examiner

*Primary Examiner*—Pedro Philogene
(74) *Attorney, Agent, or Firm*—Lerner, David, Littenberg, Krumholz & Mentlik, LLP

(57) ABSTRACT

The invention concerns a backbone osteosynthesis system, in particular for anterior fixing comprising: an elongated linking element; a vertebral screw with a threaded head; a connector comprising two branches capable of being engaged onto the screw and clamping between them the linking element; and a threaded clamping member capable of co-operating with the head for clamping the branches. The head has a threaded orifice, the clamping member comprising a threaded rod capable of being urged to be engaged in the orifice.

21 Claims, 8 Drawing Sheets

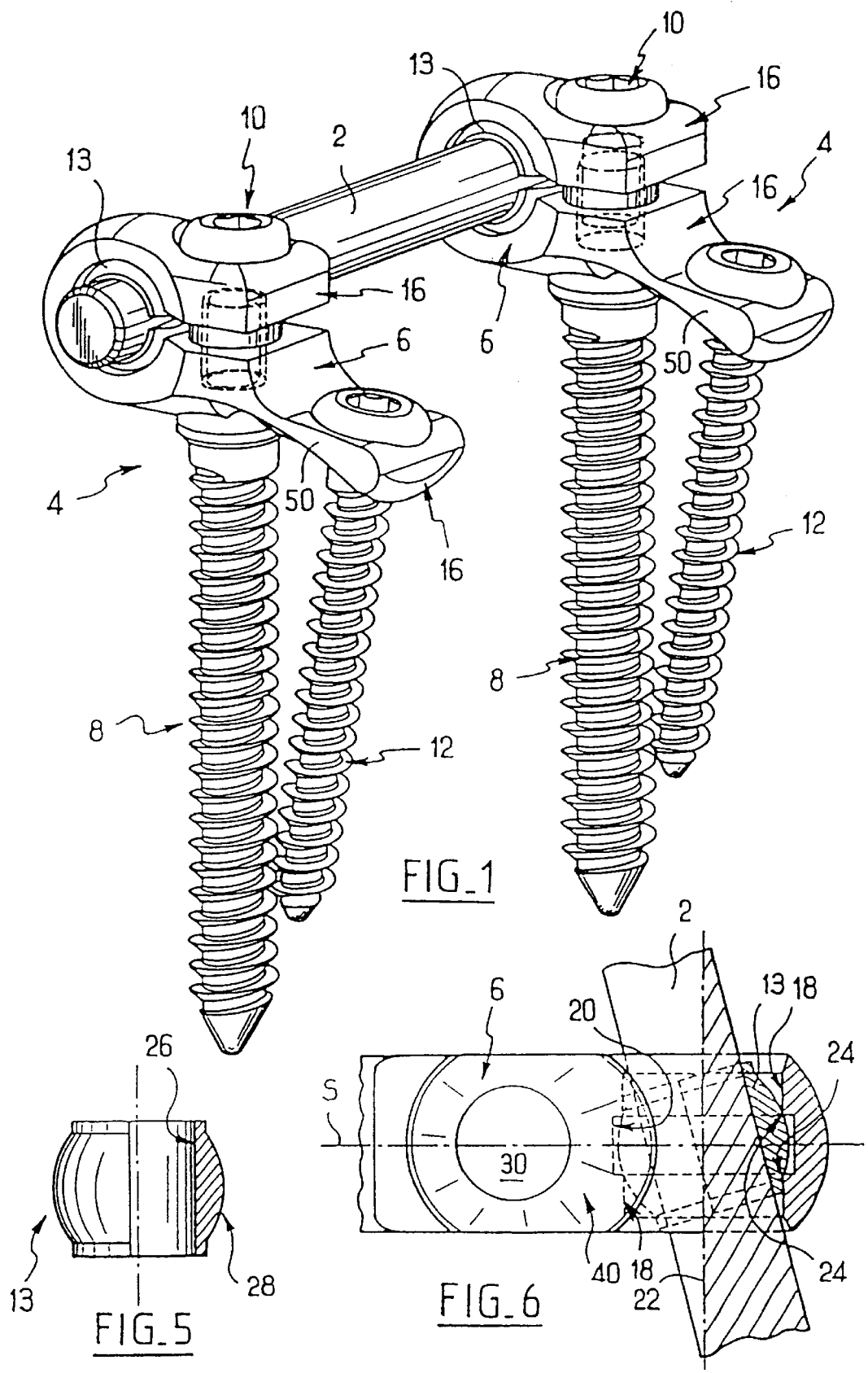

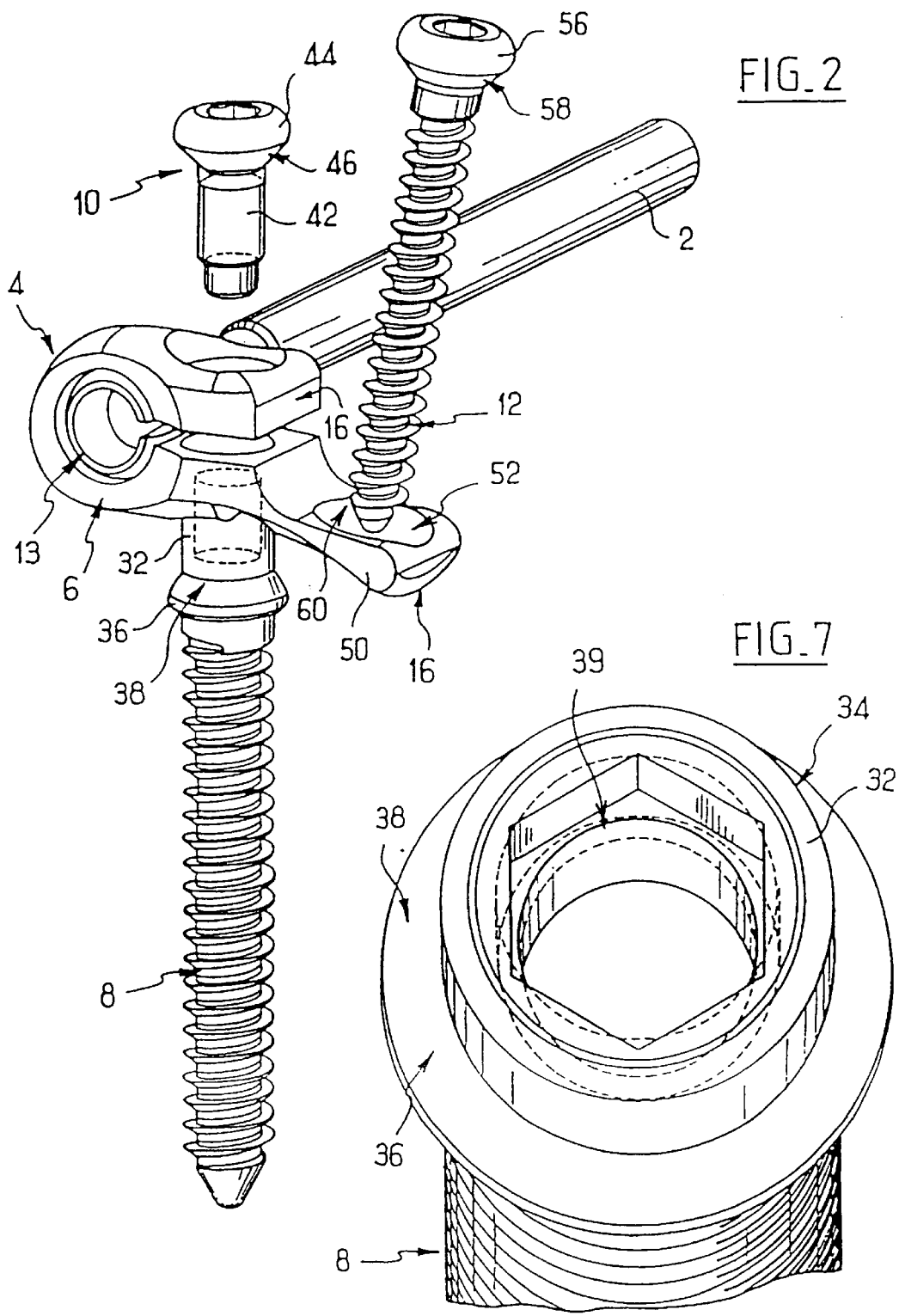

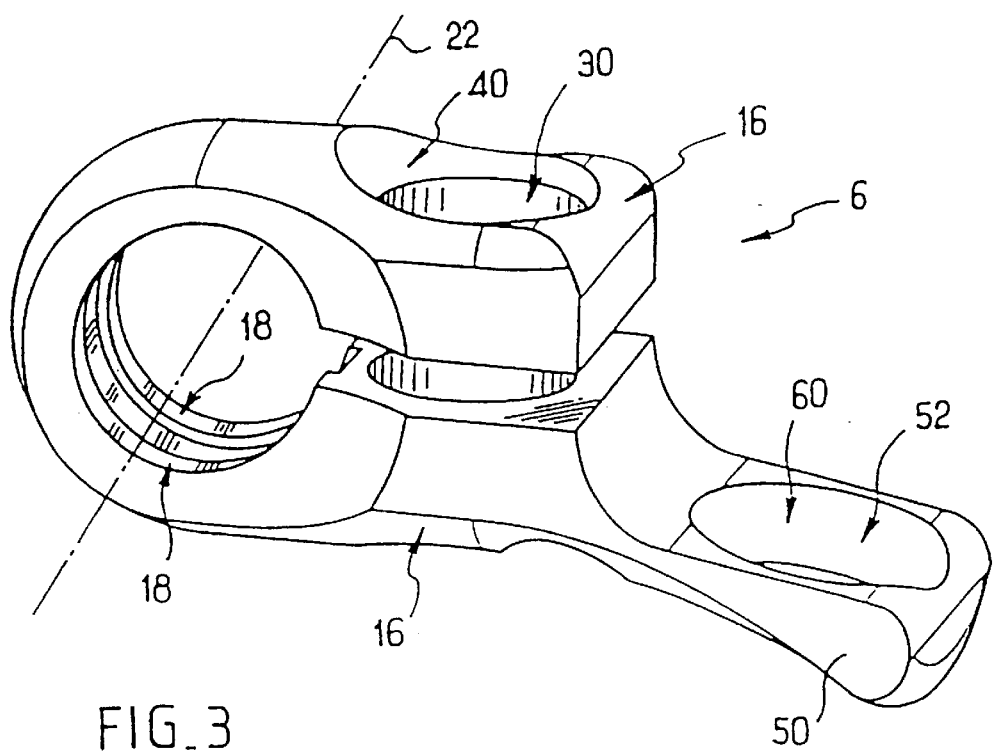
FIG_3
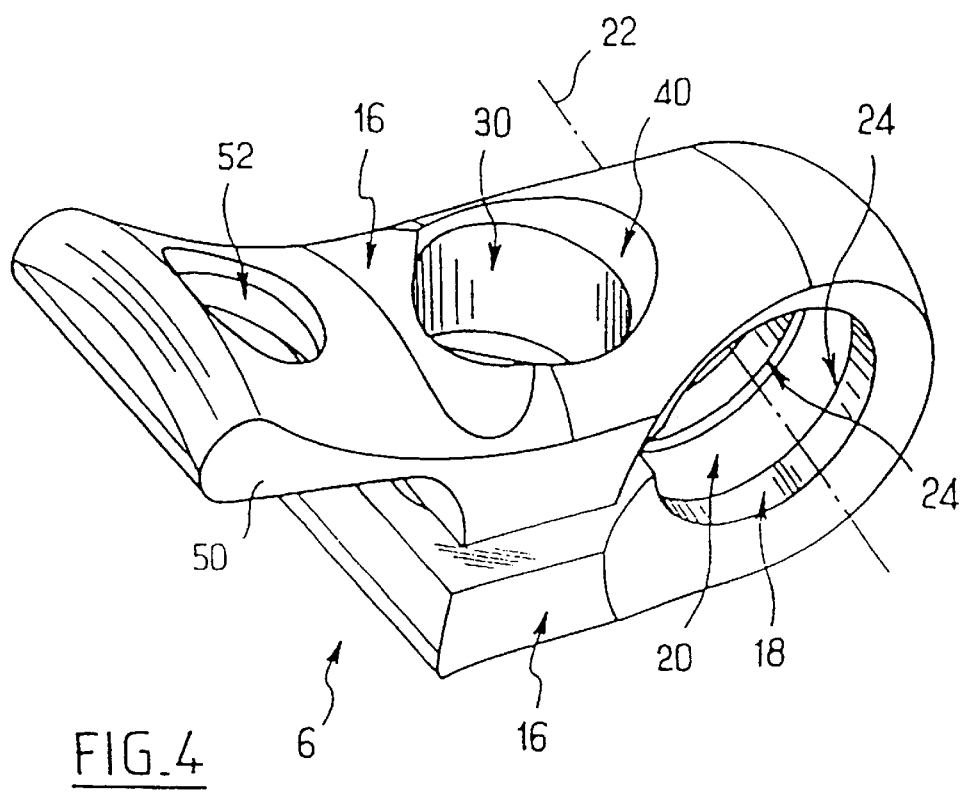
FIG_4

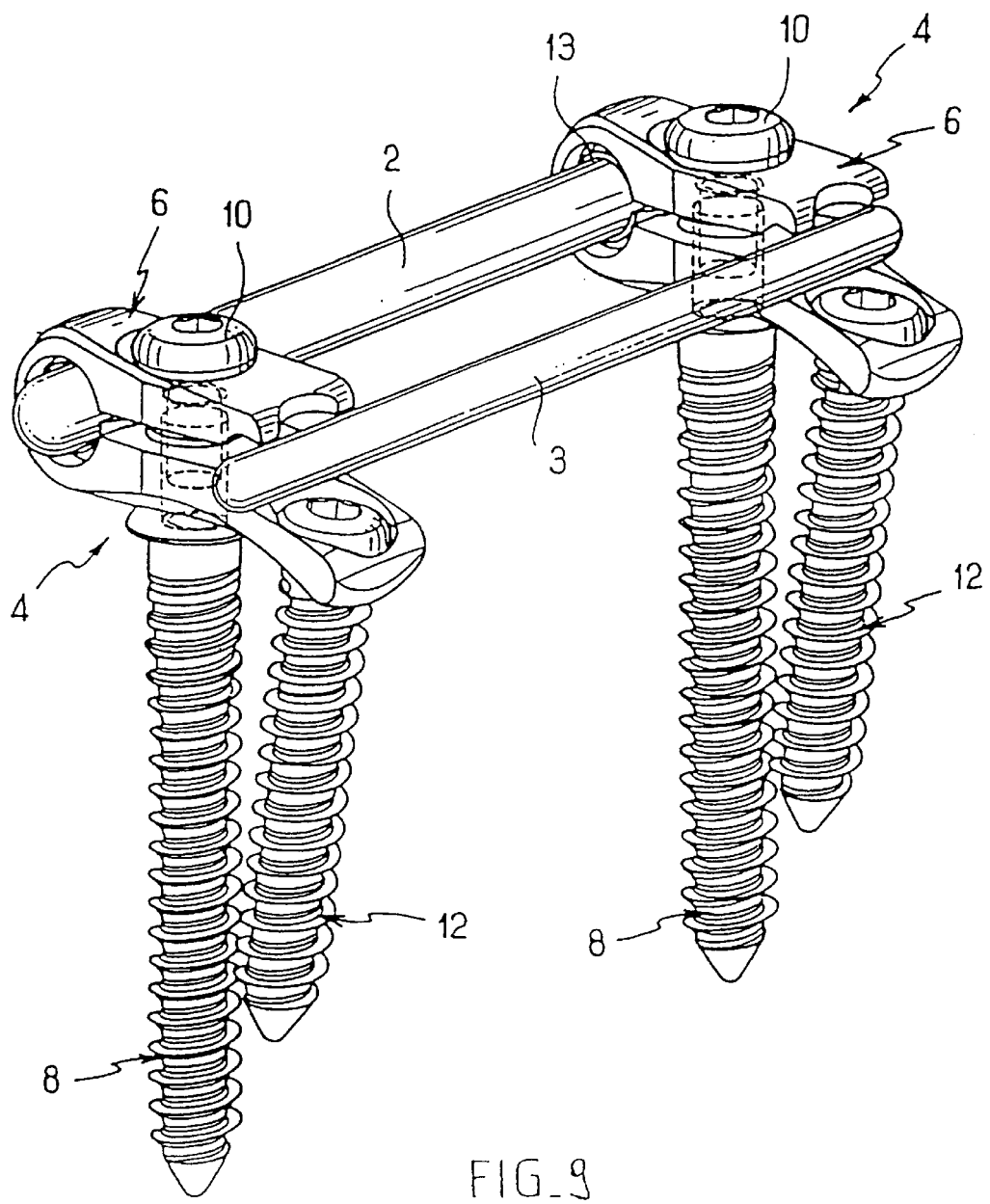
FIG_9

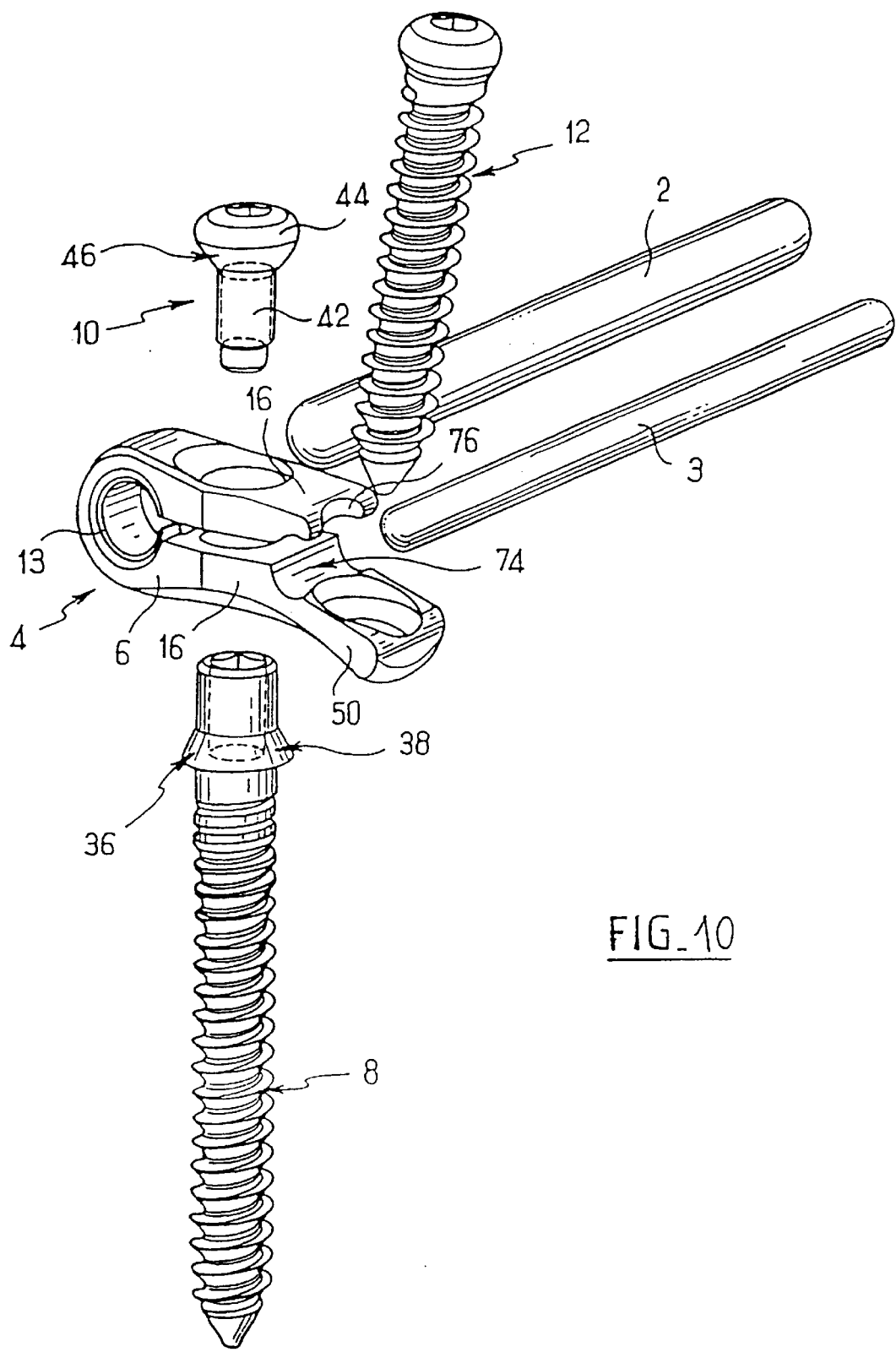
FIG_10

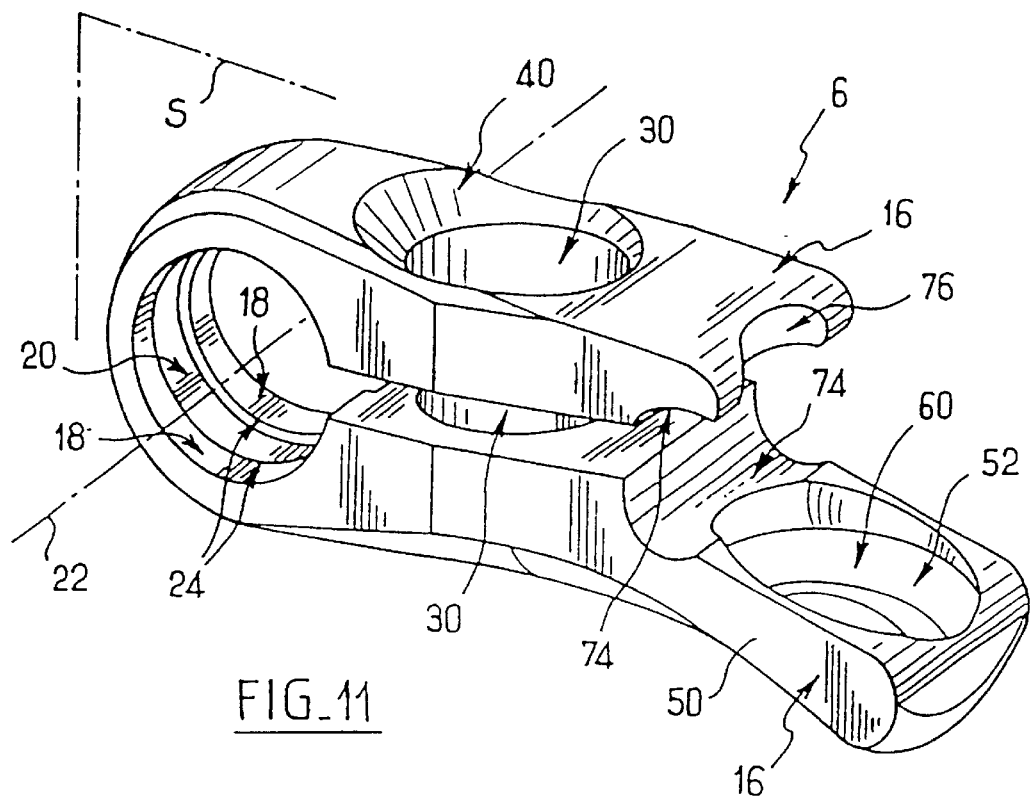
FIG_11
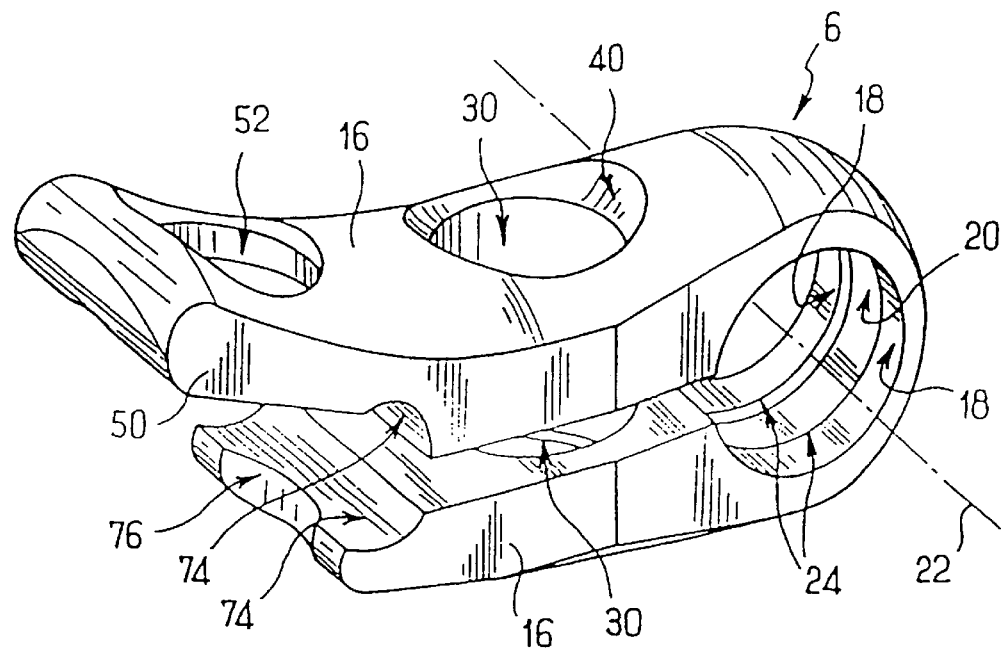
FIG_12

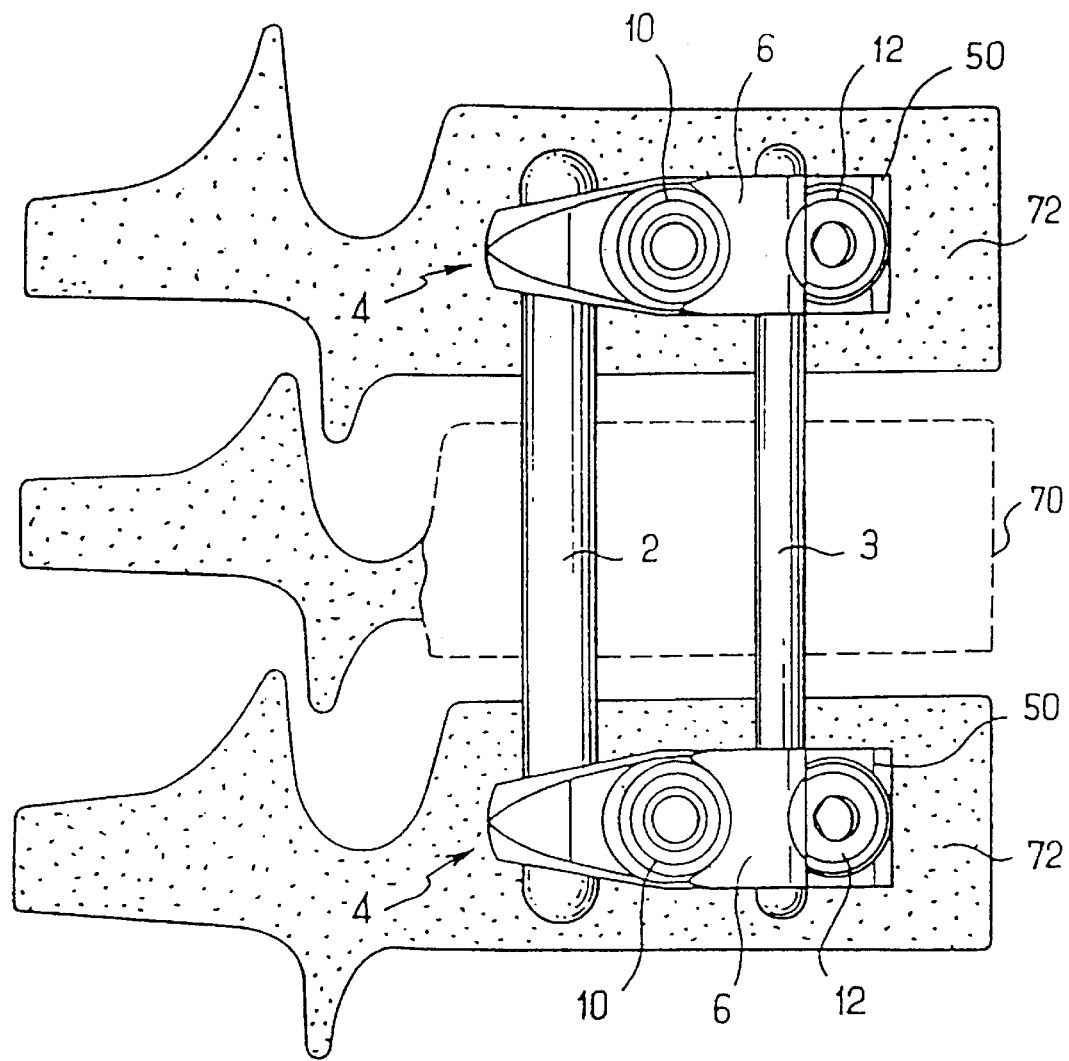
FIG_13

BACKBONE OSTEOSYNTHESIS SYSTEM WITH CLAMPING MEANS, IN PARTICLULAR FOR ANTERIOR FIXING

BACKGROUND OF THE INVENTION

The invention concerns spinal osteosynthesis systems, in particular for anterior fixation.

The document FR-2,731,344 discloses a spinal osteosynthesis system comprising a rod, a vertebral screw having a body to be anchored in a vertebra, and a head in the form of a threaded rod. The system comprises a connector with two branches which can be engaged on the screw head. A clamping nut can be fitted on the screw head in order to clamp the two branches between the base of the screw head and the nut. The rod engaged between the branches is thus clamped and immobilized.

This system has many advantages. As it includes a small number of components and is easy to put in place, it permits rapid fitting during a surgical intervention. However, the nut has a hexagonal outer profile which is necessary to permit its maneuvering and its clamping by means of a socket wrench. Now, such a profile generates numerous sharp edges and projecting corners capable of damaging the body tissues coming into contact with the nut. Similarly, it is difficult to prevent a threaded end part of the screw head from protruding from the nut upon completion of clamping. Now, this thread itself also presents projecting edges which can be damaging to the body.

SUMMARY OF THE INVENTION

An object of the invention is to reduce the number of parts projecting from the system once this has been fitted.

To achieve this object, the invention provides a spinal osteosynthesis system, in particular for anterior fixation, comprising:

- an elongate connection element;
- a vertebral screw having a threaded head;
- a connector including two branches which can be fitted on the screw and can clamp the connection element between them; and
- a threaded clamping member which can cooperate with the head in order to clamp the branches, in which the head has a threaded orifice, the clamping member comprising a threaded rod which can engage with the orifice.

Thus, the thread of the vertebral screw extends in an orifice, and the threaded orifice of the screw is closed off by the clamping member once fitting has been completed. Therefore, contact with the patient's body is no longer possible with the thread of the vertebral screw. Moreover, as the clamping member is a male piece, it is possible to form a maneuvering recess therein of polygonal profile intended to cooperate with a male instrument for maneuvering the clamping member and thereby dispense with the outer edges. This therefore also reduces the number of parts projecting from the clamping member. In addition, the connector is engaged on the head of the vertebral screw without interfering with a thread thereof. Its wedging is thus better, even before clamping by the clamping member. The connector can thus be positioned in advance on the vertebral screw in a reliable manner.

Advantageously, the clamping member has a recess of polygonal profile along a longitudinal axis of the member.

Advantageously, the clamping member comprises a head having a spherical and convex lower face, one of the said branches of the connector having a spherical and concave upper face which can be in contact with the convex face upon clamping of the branches.

It is thus possible to control the relative angular position of the connector and of the vertebral screw which is rigidly fixed to the clamping member.

Advantageously, the orifice of the vertebral screw has a recess of polygonal profile along a longitudinal axis of the screw.

This recess too, permitting maneuvering of the vertebral screw, reduces the number of projecting parts.

Advantageously, the recess extends in the thread of the orifice.

Thus, despite the presence of the thread and of the recess, it is possible for the head of the vertebral screw, and thus the system, to be given reduced dimensions.

Advantageously, the profile of the recess of the vertebral screw and the profile of the recess of the clamping member have the same shape and the same dimensions.

It is thus possible to maneuver the vertebral screw and the clamping member using one and the same male instrument, thereby reducing the equipment needed for the surgical intervention and reducing the risk of error in the choice of instruments.

Advantageously, the head of the vertebral screw has a lateral face with a smooth outer end.

Advantageously, the system comprises a second vertebral screw, one of said branches having an extension which can be engaged on the second screw.

Thus, fixation of the connector to the vertebra by means of the two screws ensures precise, stable and reliable positioning of the connector and thus of the connection element.

Advantageously, the system comprises a second elongate connection element, the connector being able to be fixed simultaneously to the two connection elements.

Thus, the presence of the two connection elements gives the system very great rigidity, without complicating its assembly, without increasing the volume of its various components (which renders it compatible with fitting via the endoscopic route), and while maintaining if need be the possibility of controlling the angular position of the connector relative to the first connection element. The system according to the invention does not require identical bending on the two connection elements. Moreover, the number of connectors can remain small.

The system according to the invention can be put into place via the endoscopic route and is designed to be fixed in the anterior position.

BRIEF DESCRIPTION OF THE DRAWINGS

Other characteristics and advantages of the invention will become more apparent from the following description of two preferred embodiments given as nonlimiting examples. In the attached drawings:

FIG. 1 is a perspective view of the system according to a first embodiment of the invention;

FIG. 2 is a partial and exploded perspective view of the system in FIG. 1;

FIGS. 3 and 4 are two perspective views, from above and below, respectively, showing one of the connectors on the system in FIG. 1;

FIG. 5 is a view, half in elevation and half in axial section, of a ring of the system in FIG. 1;

FIG. 6 is a view, partly from above and partly in section, of the connector in FIG. 3 receiving the rod;

FIG. 7 is a partial perspective view showing the head of the main screw;

FIG. 9 is a perspective view of the system according to a second embodiment of the invention;

FIG. 10 is a partial and exploded perspective view of the system in FIG. 9;

FIGS. 11 and 12 are two perspective views, from above and below, respectively, showing one of the connectors of the system in FIG. 9; and FIG. 13 shows the system from FIG. 9 fixed on vertebrae.

DESCRIPTION OF THE PREFERRED EMBODIMENTS

Figure 8:
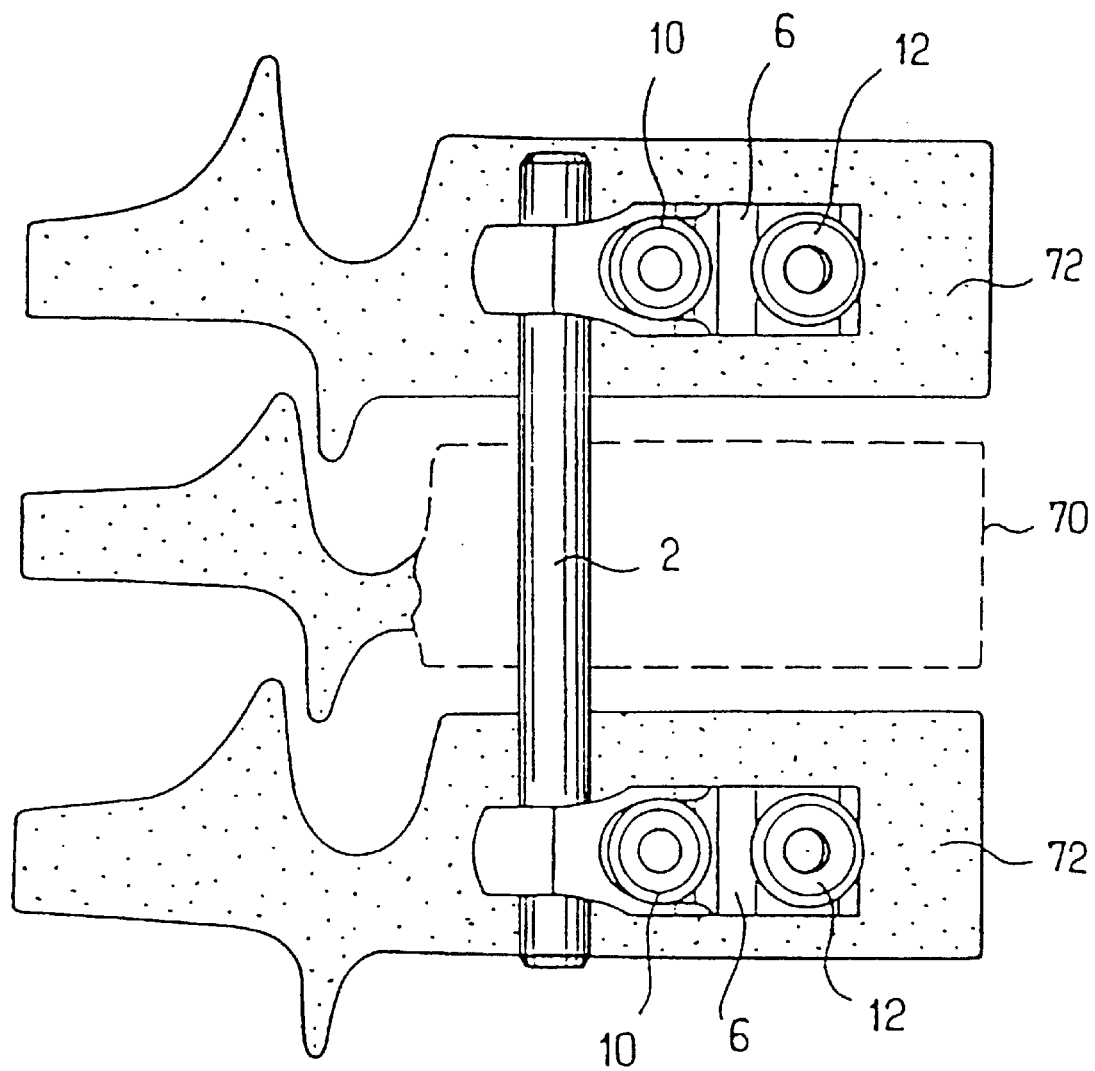
FIG. 8 shows the system from FIG. 1 fixed on vertebrae.

Referring to FIGS. 1 to 8, the system according to the invention comprises, in the first embodiment, an elongate connection rod 2 of circular cross section and several connector sub-assemblies 4 which can be fixed to the latter. Each of these sub-assemblies, of which two can be seen in FIG. 1 and of which one can be seen in FIG. 2, comprises a connector 6, a first vertebral screw or main screw 8, a clamping screw 10, a second vertebral screw or secondary screw 12, and a ring 13.

Referring to FIGS. 3 and 4, the connector 6 includes two branches 16 extending opposite to and at a distance from each other, giving the connector a general U-shaped profile. The connector 6 includes a plane of symmetry S perpendicular to the width of the branches 16 and parallel to their length. Referring to FIG. 6 at the point of origin of the branches 16 the connector has two cylindrical and coaxial inner faces 18, 20 with axis 22 perpendicular to the plane S and with different radii, the face 20 of greater radius being in two distinct parts and extending on either side of the face 18 of lesser radius, which is traversed by the plane S. At their junctions, the two faces 18, 20 form two circular edges 24 with axis 22.

The ring 13 has a cylindrical inner face 26 and a spherical outer face 28 which are coaxial. The cylindrical inner face 26 has a radius about equal to that of the rod 2 in such a way that the ring 13, slotted on one side along its axis, can be received as a sliding fit on the rod. Moreover, the ring 13 can be lodged between the branches 16 opposite the cylindrical faces 18, 20. The spherical outer face 28 of the ring has a radius which is adapted such that in this position the edges 24 of the connector 6 are in linear contact with the spherical outer face 28 of the ring 13 and serve as bearings for it. In this position, before clamping of the branches 16, the angular position of the rod 2 engaged in the ring 13 can be controlled in two mutually perpendicular planes over an amplitude of, for example, 150 on either side of a mean position of the rod in which the rod is perpendicular to the plane S.

The branches 16 have two respective smooth cylindrical openings which, in this case, are through-orifices 30 extending coaxially opposite each other. The main screw 8 is a bicortical vertebral screw and has a threaded body for this purpose, in a manner known per se. It has a head 32 having a smooth cylindrical outer face 34. At the junction between the head and the body, the screw includes an annular flange 36 having a plane lower face perpendicular to the longitudinal axis of the screw and a frustoconical upper face 38 with the narrowest cross section of the frustum situated towards the head 32 of the screw. The head 32 has a threaded orifice 39 coaxial to the body of the screw and, formed in the threaded face of the orifice 39, a noncircular shape such as a hexagon socket. The clamping screw 10 includes a threaded body 42 which is able to form a screw-nut connection with this orifice 39, and a screw head 44 in which a hexagon socket is formed. The head 44 has a spherical and convex lower outer face 46 whose narrowest cross section is situated towards the point of the screw.

One of the branches 16, which for the sake of clarity we will here call the lower branch, has an extension 50 extending in the direction away from the cylindrical faces 18, 20 of the connector. This is the branch intended to be adjacent to the vertebra. The two branches 16 are able to be engaged simultaneously on the head 32 of the main screw 8 introduced starting from the lower branch against which the upper face 38 of the flange 36 comes into abutment. The clamping screw 10 is then introduced into the head 32 of the main screw 8 starting from the upper branch 16. The tightening of the screw 10 in the head 32 of the main screw 8 causes the branches 16 to close towards each other and causes frictional blocking of the rod 2 in the chosen position relative to the connector 6.

The orifice 30 of the lower branch 16 has a lower edge, remote from the upper branch and intended to be towards the vertebra, having a concave spherical recess 40 intended to come into contact with the upper face 38 of the flange 36 in order to effect, by friction, rotational blocking of the connector 6 relative to the axis of the main screw 8. The orifice 30 of the upper branch 16 has an upper edge, remote from the lower branch and intended to be remote from the vertebra, having a concave spherical recess 40 intended to come into contact with the convex and spherical lower face 46 of the head 44 of the clamping screw 10 and making it possible to fix the latter and the main screw 8 by controlling the angular orientation of the main screw 8 relative to the connector.

The extension 50 has an opening in the form of a through-orifice 52. The lower branch 16 is curved in the area of the extension 50 in a direction away from the upper branch 16 in such a way that the axes of its orifices 30 and 52 are not quite parallel. The secondary screw 12 is a vertebral screw, here a monocortical screw, having a threaded body and a head 56 with a spherical and convex lower face 58 whose narrowest cross section is situated towards the body. Its head has a hexagon socket. The orifice 52 of the extension has an upper edge, oriented towards the other branch 16 and intended to be remote from the vertebra, having a spherical and concave recess 60 intended to come into contact with the spherical and convex lower face 58 of the head 56 of the secondary screw 12, making it possible to control the angular orientation of this screw relative to the connector 6.

Certain characteristics of the connector 6 which have not been expanded on in detail here will be found in the abovementioned related documents FR-2,731,344 and WO 96/27340 (U.S. Pat. No. 5,938,663), the teachings of which are incorporated herein by reference.

The lower branch 16 can be bent in order to accentuate or reduce its curvature for better adaptation to the shape of the anterior part of the vertebra for which it is intended. Once bent, this branch 16 is no longer stressed in flexion since it is fixed to the vertebra by two screws 8, 12 along its length. The two screws, namely the main screw 8 and the secondary screw 12, are self-tapping and include bone threads.

In an alternative embodiment, the main screw 8 does not have a hexagon socket in its threaded orifice 39, and instead the flange 36 has a hexagonal shape or has two parallel and diametrically opposite flats which can cooperate with a tightening wrench for rotating this screw 8 relative to the connector 6.

In the present example, the connector 6 is made in one piece. The different parts of the system are made of biocompatible metal.

Such a device is fitted in the following manner, with reference to FIG. 8. After exposing the affected vertebra 70 and two adjacent vertebra 72, a vertebrectomy is performed while preserving, if possible, the respective plates of these vertebrae. For each subassembly, a pilot hole is made on the lateral side of the associated vertebra 72 at an equal distance from the upper and lower plates, and at the limit of the most posterior quarter of the vertebral body. The main screw 8 is then inserted into this pilot hole as far as the limit flange 36. The connector 6 is then positioned on the said main screw 8, blocked in translation by the conical face 38 of the said main screw 8 matching the recess 40 of the connector 6. The fit of the connector 6 on the vertebra is then checked and can be adjusted by withdrawing the said connector in order to bend the lower branch 16 which is its most anterior part.

The secondary screw 12 is then screwed relative to the main screw 8 into the second orifice 52 of the lower branch 16 until the spherical seat 60 of the extension, provided for this purpose, comes into contact with the spherical part 58 of the said secondary screw 12. It is desirable to position the connector 6 as parallel as possible to the plates.

After the two adjacent vertebrae 72 have been thus equipped, the rod 2 is positioned in the rings of the connectors 6 and its angular position on each sub-assembly is controlled. Final clamping is effected by virtue of the clamping screw 10 which is inserted into the main screw 8 and thereby compresses the connector 6 in order to clamp the rod.

In the second embodiment illustrated in FIGS. 9 to 13, the system is very similar to that of the first embodiment. However, it is distinguished by the presence of a second elongate connection rod 3 or secondary rod of circular cross section, and by the adaptation of the connector 6 for receiving this second rod. The ring 13 is received on the first rod or main rod 2.

The two connection rods 2, 3 each have a profiled rectilinear shape, the profile here being circular. The secondary rod 3 has a cross section, transverse to its longitudinal axis, having a diameter smaller than that of the main rod 2. The main rod 2 will, for example, have a diameter of 6 mm. The diameter of the secondary rod 3 will, for example, be between 30% and 80% of the diameter of the main rod 2. This small diameter allows the surgeon to choose the curvature of the secondary rod 3 corresponding to that of the level of the spine which is being operated on. By contrast, since the rings 13 allow relative angular positioning of the two connectors 6, the main rod 2 does not have to be bent. It can thus have a substantial diameter in order to be very robust.

The branches 16 of the connector have respective cylindrical recesses or jaws 74 formed in the faces of the branches opposite each other. The recesses 74 extend opposite each other and have axes parallel to each other and perpendicular to the plane of symmetry S.

On the upper branch 16, the recess 74 extends at a free end of the branch such that the orifice 30 is interposed between the faces 18, 20, on the one hand, and the recess 74 on the other. On the lower branch 16, the recess 74 extends between the two orifices 30 and 52, at the origin of the extension 50. It is contiguous with the orifice 52 so that it engages on its edge 60.

The secondary rod 3 is intended to be received in the recess 74 of the lower branch 16 in a unique angular position relative to the connector, perpendicular to the plane of symmetry S. When the two branches 16 are clamped in the direction of each other, the recess 74 of the upper branch comes into contact with the secondary rod 3 which is thus in surface contact with each of the two recesses, which effect frictional blocking of the secondary rod 3 relative to the connector 6, which are thereby rigidly fixed to each other.

The secondary rod 3 is placed in the recess 74 of the lower branch after the secondary screw 12 has bee introduced into the orifice 52. The position of the recess 74 of the lower branch is such that the secondary rod 3 then extends in the trajectory of the head of the secondary screw 12 for its disengagement from the connector and its exit from the orifice 52. Consequently, once the secondary rod 3 has been fixed to the connector, secondary screw 12 can no longer be separated from the connector.

The upper branch 16 of the connector has at its free end a notch 76 which engages on the recess 74 with which it is contiguous and facilitates maneuvering of the secondary screw 12 by means of an instrument despite the space occupied by the upper branch.

The system according to the second embodiment is fitted in a similar way to the system of the first embodiment. The placement of the main screw 8 and of the secondary screw 12 remains unchanged.

After the two adjacent vertebrae 72 have been equipped, the main rod 2 is positioned in the rings 13 of the connectors 6 and the angular position of each sub-assembly 4 relative to this rod 2 is controlled. The secondary rod 3 is then introduced into the recesses 74 of the connectors 6 after it has first been bent manually to obtain the curvature required for the corresponding level of the spine. In the event of an error, this rod 3 can be removed in order to correct its curvature and then put back in place. FIG. 9 shows the system before the clamping of the branches. Final clamping is effected by virtue of the clamping screw 10 which is inserted into the main screw 8 and thereby compresses the connector 6 in order to clamp its two branches 16 towards each other. During this clamping, the clamping force is directed first on the main rod 2 via the ring 13, until the recess 74 of the upper branch comes into contact with the secondary rod 3. Thereafter, the clamping force is distributed on the two rods 2, 3. Thus, the reaction at the level of the pairing of main screw 8 and clamping screw 10 is substantially coaxial to these.

When the system is in place, the connectors 6, of which there are at least two, are each rigidly and simultaneously fixed to the same main rod and secondary rod.

In each of these embodiments, the characteristics relating to the association of the first screw 8 with the clamping screw 10 will be able to be implemented independently of the presence of the extension 50 and of the second screw 12. Although less advantageous, the extended branch can be the one which is intended to be farthest from the vertebra.

The characteristics relating to the presence of the two vertebral screws on the connector will be able to be implemented independently of those relating to the presence of the main and secondary rods, and vice versa.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A spinal osteosynthesis system, in particular for anterior fixation, comprising:

an elongate connection element;

a vertebral screw having a threaded shank and an internally threaded head;

a connector including a first and second branch, said first branch having a bone contacting surface with an opening surrounded by a concave recess which can be fitted on the screw and an opening between said first and second branches for securing the connection element between them; and a threaded clamping member which can cooperate with the head in order to clamp the branches onto the connection element, the screw head having a threaded portion, the clamping member comprising a threaded element which can engage the threads of the screw head, wherein the clamping member comprises a head having a spherical and convex lower face, a second of said branches of the connector having a concave recess around an opening in the upper face which can be in contact with the convex lower face of the clamping member upon clamping of the branches.

2. The system according to claim 1, wherein the clamping member has a recess of polygonal profile along a longitudinal axis of the member.

3. The system according to claim 1 or 2, wherein the recess of the first branch of the connector having a spherical and concave upper face which contacts a spherical and convex face of the vertebral screw upon clamping of the branches.

4. The system according to claim 1, wherein the threaded portion of the head of the vertebral screw has a recess of polygonal profile extending along a longitudinal axis of the screw.

5. The system according to claim 4, wherein the recess extends in the thread of the threaded portion.

6. A system according to claim 2 or claim 4, wherein the profile of the polygonal recess of the vertebral screw and the profile of the recess of the clamping member have the same shape and the same dimensions.

7. The system according to claim 1, wherein the head of the vertebral screw has a lateral face with a smooth outer end.

8. The system according to claim 1 further comprising a second vertebral screw, one of the said branches having an extension which can receive the second screw.

9. The system according to claim 1 further comprising a second elongate connection element, the connector being able to be fixed to the two connection elements.

10. A spinal system comprising:

a first generally U-shaped connector, a base of said U-shaped connector for receiving a rod extending along an axis, said connector having a first bone contacting branch and a second branch extending from said rod receiving base forming the legs of the U, said branches each having first openings therein having a concave surface formed therearound;

a first vertebral screw having a threaded shank and a head with an internally threaded portion, said head engaging said first branch in the area of said first opening therein, said screw having a convex surface for engaging a bone facing concave surface on said first branch; and a first threaded clamping member engaging said second branch in the area of said first opening therein, said clamping member threadably engaging said internally threaded head of said vertebral screw within said openings in said first and second branches, said clamping member having a convex surface formed thereon for engaging the concave surface on said second branch.

11. The spinal system as set forth in claim 10, wherein said vertebral screw and said threaded clamping member include polygonal drive surfaces.

12. The spinal system as set forth in claim 10, wherein said first branch includes a second opening located at a greater distance from said base than said first opening for receiving a bone screw.

13. The spinal system as set forth in claim 12, wherein said first branch has a rod receiving recess between said first and second openings.

14. The spinal system as set forth in claim 13, wherein said second branch has a portion for engaging a rod located in said rod receiving recess in said first branch.

15. The spinal system as set forth in claim 10, wherein said system further comprises:

a second generally U-shaped connector, a base of said U-shaped connector for receiving a rod extending along an axis, said second connector having a first and a second branch extending from said rod receiving base forming the legs of the U, said branches each having first openings therein;

a second vertebral screw having a threaded shank and a head with an internally threaded portion, said head engaging said first branch of said second connector in the area of said first opening therein;

a second threaded clamping member engaging said second branch of said second connector in the area of said first opening therein, said clamping member threadably engaging said internally threaded head of said vertical screw within said openings in said first and second branches of said second connector; and a rod extending between said first and second U-shaped connectors.

16. A method for linking a first and a second vertebrae comprising:

inserting first and second vertebral screws, each having a threaded shank and a part spherical head with an internally threaded portion into respective first and second vertebrae;

placing a generally U-shaped connector having an opening therein for receiving said screw head on each of said first and second vertebral screws, a base of each of said U-shaped connectors for receiving a rod, a first and second branch of each said connectors extending from said rod receiving base, said first branch of each of said connectors having a bone contacting surface with a recess around said opening for respectively engaging the head of said first and second vertebral screws;

controlling the angular orientation of the vertebral screw by the engagement of said part spherical surface on each of said vertebral screw heads with said recess in said first branch of said connector;

inserting a rod in said rod receiving bases of each of said U-shaped connectors to link said connectors; and clamping said first and second branches of each of said U-shaped connectors together by inserting a threaded clamping member engageable with said second branch of each of said connectors into said internal threaded portion of said heads of said first and second vertebral screws.

17. The method as set forth in claim 16 further comprising inserting a second vertebral screw into said first and second vertebrae through an opening in said first branch of each U-shaped connector.

18. The method as set forth in claim 17 further comprising clamping a second red between said U-shaped connectors at a position on each connector between said first and second screws.

19. The method as set forth in claim 16 further comprising the removal of a diseased vertebrae intermediate said first and second vertebrae.

20. The method as set forth in claim 16 wherein each of said second branches of said connector has an opening therethrough and an outwardly facing surface having a recess surrounding said opening, said recess engaging a head on said threaded clamping member.

21. The method as set forth in claim 20 wherein said recesses have a concave shape and said heads of said first and second screws and a head of said clamping members have a convex shape.

* * * * *

UNITED STATES PATENT AND TRADEMARK OFFICE
CERTIFICATE OF CORRECTION

PATENT NO. : 6,565,569 B1
DATED : May 20, 2003
INVENTOR(S) : Richard Assaker et al.

It is certified that error appears in the above-identified patent and that said Letters Patent is hereby corrected as shown below:

<u>Title page, Item [54] and Column 1, line 2,</u>
Cancel ",".

<u>Column 3,</u>
Line 49, "150" should read -- 15º --.

<u>Column 9,</u>
Line 2, "red" should read -- rod --.

Signed and Sealed this

Sixteenth Day of September, 2003

JAMES E. ROGAN
*Director of the United States Patent and Trademark Office*